United States Patent
Brewer et al.

(10) Patent No.: US 11,992,255 B2
(45) Date of Patent: May 28, 2024

(54) SURGICAL ASSEMBLY AND SYSTEM, AND A DC VOLTAGE COMPENSATION CIRCUIT

(71) Applicant: ALESI SURGICAL LIMITED, Cardiff (GB)

(72) Inventors: Jason Brewer, Cardiff (GB); Dominic Griffiths, Cowbridge (GB); Francis Kweku Egyin Amoah, Cardiff (GB); George Hearn, Cardiff (GB); Robert Rudolf, Cambridge (GB); Matt Neighbour, Cambridge (GB); Eugene Van Wyk, Cambridge (GB)

(73) Assignee: ALESI SURGICAL LIMITED, Cardiff (GB)

( * ) Notice: Subject to any disclaimer, the term of this patent is extended or adjusted under 35 U.S.C. 154(b) by 398 days.

(21) Appl. No.: 16/614,655

(22) PCT Filed: May 21, 2018

(86) PCT No.: PCT/GB2018/051372
§ 371 (c)(1),
(2) Date: Nov. 18, 2019

(87) PCT Pub. No.: WO2018/211292
PCT Pub. Date: Nov. 22, 2018

(65) Prior Publication Data
US 2020/0197069 A1    Jun. 25, 2020

(30) Foreign Application Priority Data
May 19, 2017    (GB) .................................. 1708081

(51) Int. Cl.
*A61B 18/12* (2006.01)
*A61B 18/00* (2006.01)

(52) U.S. Cl.
CPC .... *A61B 18/12* (2013.01); *A61B 2018/00595* (2013.01); *A61B 2018/00601* (2013.01);
(Continued)

(58) Field of Classification Search
CPC .......... A61B 18/12; A61B 2018/00595; A61B 2018/00601; A61B 2018/122;
(Continued)

(56) References Cited

U.S. PATENT DOCUMENTS

2005/0248391 A1    11/2005   Itoh
2008/0287948 A1*  11/2008   Newton ............. A61B 18/1206
                                                                           606/50
(Continued)

FOREIGN PATENT DOCUMENTS

EP    2168523 A2    3/2010
GB    2496382 A     5/2013
(Continued)

OTHER PUBLICATIONS

PCT International Search Report and Written Opinion, PCT/GB2018/051372, dated Oct. 5, 2018, 21 pages.
Intellectual Property Office, Search Report and Examination Opinion, GB1708081.3, dated Nov. 6, 2017, 5 pages.
Intellectual Property Office, Search Report, GB1808330.3, dated Nov. 14, 2018, 5 pages.

*Primary Examiner* — Eun Hwa Kim
*Assistant Examiner* — Catherine C. Premraj
(74) *Attorney, Agent, or Firm* — Quarles & Brady LLP

(57) ABSTRACT

A surgical assembly and system are disclosed. The system comprises a first generator for generating a first signal for use in generating an electrical field proximate a site of a surgical procedure for removing particles suspended proximate the surgical site. The assembly further comprises a surgical tool comprising a tool-piece communicatively couplable with the first generator and a second generator, the second generator being arranged to generate a second signal for use in cutting or cauterizing biological tissue of the
(Continued)

patient during the surgical procedure, the assembly further comprising a switching assembly for switching the application of the first signal and second signal to the tool-piece and a controller for controlling the application of the first signal and second signal to the tool-piece. A DC voltage compensation circuit is also disclosed for varying a voltage output by an DC generator to a tool-piece, for maintaining a substantially constant voltage difference between a distal end of the tool-piece and patient tissue.

9 Claims, 7 Drawing Sheets

(52) U.S. Cl.
CPC . *A61B 2018/122* (2013.01); *A61B 2018/1266* (2013.01); *A61B 2018/1273* (2013.01); *A61B 2562/0257* (2013.01)

(58) Field of Classification Search
CPC .... A61B 2018/1266; A61B 2018/1273; A61B 2562/0257
See application file for complete search history.

(56) References Cited

U.S. PATENT DOCUMENTS

| | | |
|---|---|---|
| 2012/0062195 A1 | 3/2012 | Ting |
| 2012/0067212 A1* | 3/2012 | Warren .................... A61N 1/20 95/57 |
| 2012/0150170 A1* | 6/2012 | Buysse .............. A61B 18/1445 606/34 |
| 2016/0022350 A1* | 1/2016 | Yuan .................... A61B 18/042 606/34 |
| 2016/0054749 A1 | 2/2016 | Fujiwara et al. |
| 2016/0341952 A1* | 11/2016 | Narita .................. H04N 5/2256 |
| 2017/0086915 A1* | 3/2017 | Batchelor .......... A61B 18/1206 |

FOREIGN PATENT DOCUMENTS

| | | |
|---|---|---|
| JP | 2012032940 A | 2/2012 |
| WO | 201101048 A2 | 1/2011 |
| WO | 2016024130 A1 | 2/2016 |
| WO | 2017053945 A1 | 3/2017 |

* cited by examiner

SURGICAL ASSEMBLY AND SYSTEM, AND A DC VOLTAGE COMPENSATION CIRCUIT

CROSS-REFERENCE TO RELATED APPLICATIONS

This application represents the national stage entry of PCT International Application No. PCT/GB2018/051372 filed on May 21, 2018 and claims priority to Great Britain Patent Application 1708081.3 filed on May 19, 2017. The contents of these applications are hereby incorporated by reference as if set forth in their entirety herein.

The present invention relates to a surgical assembly and system, and a DC voltage compensation circuit.

Particulate matter in aerosol form is commonly encountered during surgical procedures. For example, it can be either utilized to deliver a therapeutic agent or can be experienced as a result of performing a surgical procedure. Examples of particulate-based therapeutic agents are the delivery of agents for effecting rapid clotting of blood or for treating diseases such as cancer. A common example of particulate matter created as a result of performing a surgical procedure is that experienced when using "energy-based" surgical instruments. Energy-based surgical instruments are powered in some manner in order to deliver a therapeutic effect such as cutting or coagulating tissue. Although there are several modes of action such as radiofrequency (RF), ultrasonic and laser, all of these energy-based instruments create particulate matter as a by-product of their mode of action.

Particulate matter created in an aerosol form by energy-based instruments is problematic for at least two reasons. Firstly, it rapidly obscures the visual field of the surgeon, and therefore slows the surgical procedure and creates risk of accidental harm to the patient caused by poor visibility. Secondly there are concerns that long-term exposure to particulate matter created by these instruments may represent a hazard for healthcare workers. Historically vacuum-based systems have been used to extract the aerosol particulate matter from the surgical field. However, because this is a dilution-based process it is inefficient at rapidly removing the particulate matter and improving the visual field quality. In addition to this, and in the case of surgical procedures that require gas insufflation to create an operative space, such as laparoscopic surgery for example, the resulting exchange of gas dries and desiccates tissue which has a detrimental effect for the patient. As a result of this and the fact that vacuum-based systems are loud and cumbersome, the adoption of vacuum-based systems has been poor.

WO2011/010148 discloses an alternative approach for managing particulate matter in surgical procedures via an apparatus for the reduction and removal of surgical smoke and other aerosol particulates generated during electrosurgical procedures. The apparatus generates a stream of electrons from a pointed electrode placed near the surgical site, such as within an abdominal cavity, and the electrons emitted from the electrode attach themselves to the aerosol particles suspended nearby. The apparatus further establishes an electrical potential difference between the electrode and the patient for attracting the ionized particles away from the surgical site and thus improving the surgeon's view of the site.

However, the electrode that is deployed into the abdomen for example, requires an additional incision within the abdominal wall which is undesirable. The effectiveness of the apparatus is also dependent on the positioning of the electrode relative to the site of surgery and other surgical instruments, and is thus subject to the surgeon's experience and skill.

We have now devised a surgical assembly and system which address at least some of the above-mentioned limitations.

In accordance with a first aspect of the present invention there is provided a surgical assembly comprising a switching assembly which is arranged to receive a first signal for use in generating an electrical field proximate a site of a surgical procedure for removing particles suspended proximate the surgical site, and a second signal for use in cutting, sealing or cauterizing tissue of the patient during the surgical procedure, the assembly further comprising a surgical tool comprising a tool-piece, the switching assembly being arranged to switch the application of the first signal and second signal to the tool-piece, and a controller for controlling the application of the first signal to the tool-piece during a first time interval and the application of the second signal to the tool-piece for a second time interval, wherein the controller comprises a timing arrangement configured to time the application of the first signal to the tool-piece following the second interval, such that the first and second intervals are non-overlapping intervals.

In an embodiment, the first and second signals are separated by a third interval during which the first and second signals are removed from the tool-piece.

In an embodiment, the assembly further comprises a first generator for generating the first signal, the tool-piece being communicatively couplable with the first generator. The assembly further comprises a sensing arrangement for sensing the second signal from the second generator, as it passes through the controller, the sensing arrangement being arranged to output a sensing signal to the controller in dependence of the sensed second signal. It is envisaged that this sensing arrangement will be particularly useful for situations where the second signal comprises an ultrasonic or laser signal, for example. The first interval corresponds to an interval during which the second signal is below a second threshold value and the second interval corresponds to an interval during which the first signal is below a first threshold value. The first and second threshold values preferably correspond to first and second signal values below which the first and second signals are unable to provide their surgical function of particulate clearing, and cutting, sealing or cauterizing, respectively.

In an embodiment, the controller comprises at least one actuator which is arranged to control the application of the first and second signals to the tool-piece. The actuator may comprise a hand switch disposed upon the surgical tool. Alternatively, the actuator may comprise a foot-actuated actuator. In a further alternative, the actuator may be disposed remotely from the surgical site, such as in a robotic procedure, for example.

In an embodiment, the controller comprises an override actuator for activating the first signal. At any time during the first time interval, or following the first interval, namely during a time when the first signal is not applied to the tool-piece, but before the second interval commences, namely before the second signal is applied to the tool-piece, then upon actuating the override actuator, the controller is arranged to further apply the first signal to the tool-piece while the override actuator is activated. It is envisaged that this facility will be useful for surgeons who wish to clear large accumulations of suspended particles, including surgical smoke.

In an embodiment, the timing arrangement is arranged to delay the switching of the first and second signals to the tool-piece, following an instruction from the controller, to allow any residual capacitance voltages and inductance currents within the first and second signal generators to dissipate or fall below the respective threshold values.

In an embodiment, the first generator comprises a first electrical generator and a first electrical pole of the first generator is electrically couplable with the tool-piece and a second electrical pole of the first generator is electrically couplable with the patient. The second electrical pole may be electrically couplable with the patient via an adhesive pad and electrically conducting gel. The first and second generator may share the same second electrical pole.

In an embodiment, the first electrical generator is configured to generate a direct current signal, to establish a directional electrical field between the tool-piece and biological tissue of the patient. The assembly may further comprise a second generator for generating the second signal. In an embodiment, the second generator comprises a second electrical generator which is configured to generate radio-frequency alternating current signal.

In an embodiment, the tool-piece comprises at least one ion-generating centre. The ion-generating centre may comprise a pointed distal end of the tool-piece and/or a serrated portion of the tool-piece, for example.

In an embodiment, the tool-piece comprises a linear configuration, a J-shape configuration, an L-shape configuration or may comprise a blade, or a forceps comprising a pair of opposing jaws, for example.

In an embodiment, the tool-piece is detachably couplable with the surgical tool. The tool-piece may comprise a disposable, single-use tool-piece, for example. The tool may also comprise a disposable, single use tool, for example.

In an embodiment, the surgical tool comprises a housing, at least a portion of which serves as a handle. Preferably, the controller is disposed within the housing.

In an embodiment, the first and second signals are communicated to the tool-piece via a connecting cable, which is arranged to electrically couple with the first generator via a cable connector.

In an embodiment, any residual capacitive charge accumulated during the preceding first or second interval is allowed to discharge or dissipate during the third interval. In an embodiment, the assembly further comprises at least one resistor for enabling the discharge or dissipation of residual charge.

In an embodiment, the assembly further comprises a proximity sensor for sensing a proximity of a distal end of the tool-piece to patient tissue.

In an embodiment, the assembly further comprises a voltage compensation circuit for maintaining a substantially constant voltage difference between a distal end of the tool-piece and patient tissue independently of a separation between the tool-piece and the patient tissue. The voltage compensation circuit is arranged to maintain the substantially constant voltage difference as the current passing between the tool-piece and patient tissues varies between 0-100 µA, preferably 0-50 µA and more preferably 0-10 µA.

In an embodiment, the voltage compensation circuit comprises a resistor arrangement electrically couplable with an output of the first generator and a processor which is arranged to receive as input a target voltage and a signal representative of an electrical current flowing through the resistor arrangement, the processor being arranged to process the signal and increase the voltage output from the first generator by an amount corresponding to a voltage drop across the resistor arrangement.

In an embodiment, the assembly further comprises an analogue closed loop circuit for closed loop control of the current output from the first generator. The analogue closed loop circuit is arranged to limit the current flowing from the first generator to a maximum value of 100 µA.

In accordance with a second aspect of the present invention, there is provided a surgical system comprising a surgical assembly of the first aspect, a first generator for generating a first signal for use in generating an electrical field proximate a site of a surgical procedure for removing particles suspended proximate the surgical site resulting from the surgical procedure, and a second generator for generating a second signal for use in cutting or cauterizing biological tissue of the patient during the surgical procedure.

In accordance with a third aspect of the present invention, there is provided an DC voltage compensation circuit for varying a voltage output by an DC generator to a tool-piece, for maintaining a substantially constant voltage difference between a distal end of the tool-piece and patient tissue independently of an electrical impedance arising from a separation between the tool-piece and the patient tissue, the circuit comprising a resistor arrangement electrically couplable with an output of the DC generator and a processor which is arranged to receive as input a target voltage and a signal representative of an electrical current flowing through the resistor arrangement, the processor being arranged to process the signal and increase the voltage output from the electrosurgical generator by an amount corresponding to a voltage drop across the resistor arrangement.

In accordance with a fourth aspect of the present invention, there is provided a process for applying a first signal and a second signal to a tool-piece, the first signal being for use in generating an electrical field proximate a site of a surgical procedure for removing particles suspended proximate the surgical site, and the second signal being for use in cutting, sealing or cauterizing tissue of the patient during the surgical procedure, the process comprising applying the first signal to the tool-piece during a first time interval and applying the second signal to the tool-piece for a second time interval, the processing comprising timing the application of the first signal to the tool-piece following the second interval, such that the first and second intervals are non-overlapping intervals Further features of the surgical system or DC voltage compensation circuit or process may comprise one or more of the features of the surgical assembly described above.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments.

Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

The invention may be performed in various ways, and, by way of example only, embodiments thereof will now be described, reference being made to the accompanying drawings in which:

FIGS. 1b-1f are schematic illustrations of alternative tool-pieces for use in the tool of the assembly of FIG. 1a;

Figure 1A:
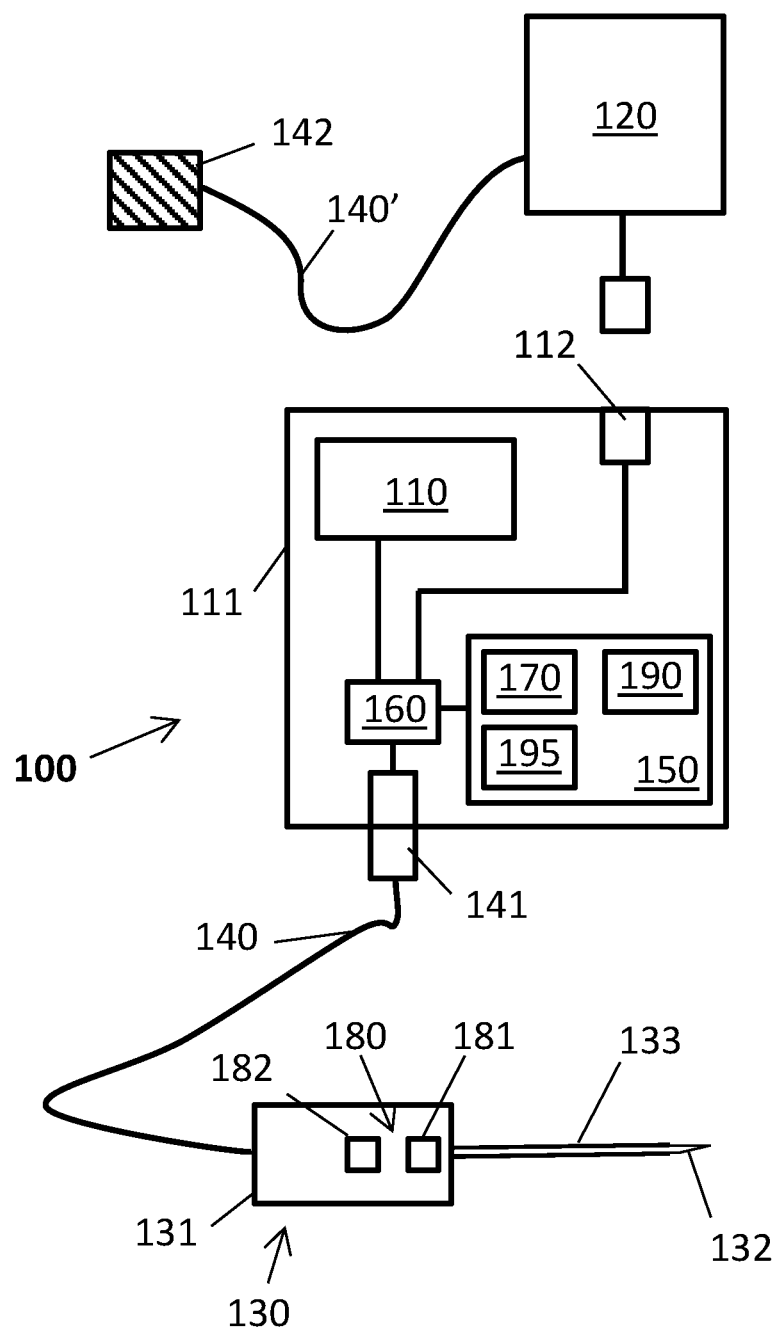
FIG. 1a is a schematic illustration of a surgical assembly according to an embodiment of the present invention.
Figure 1:
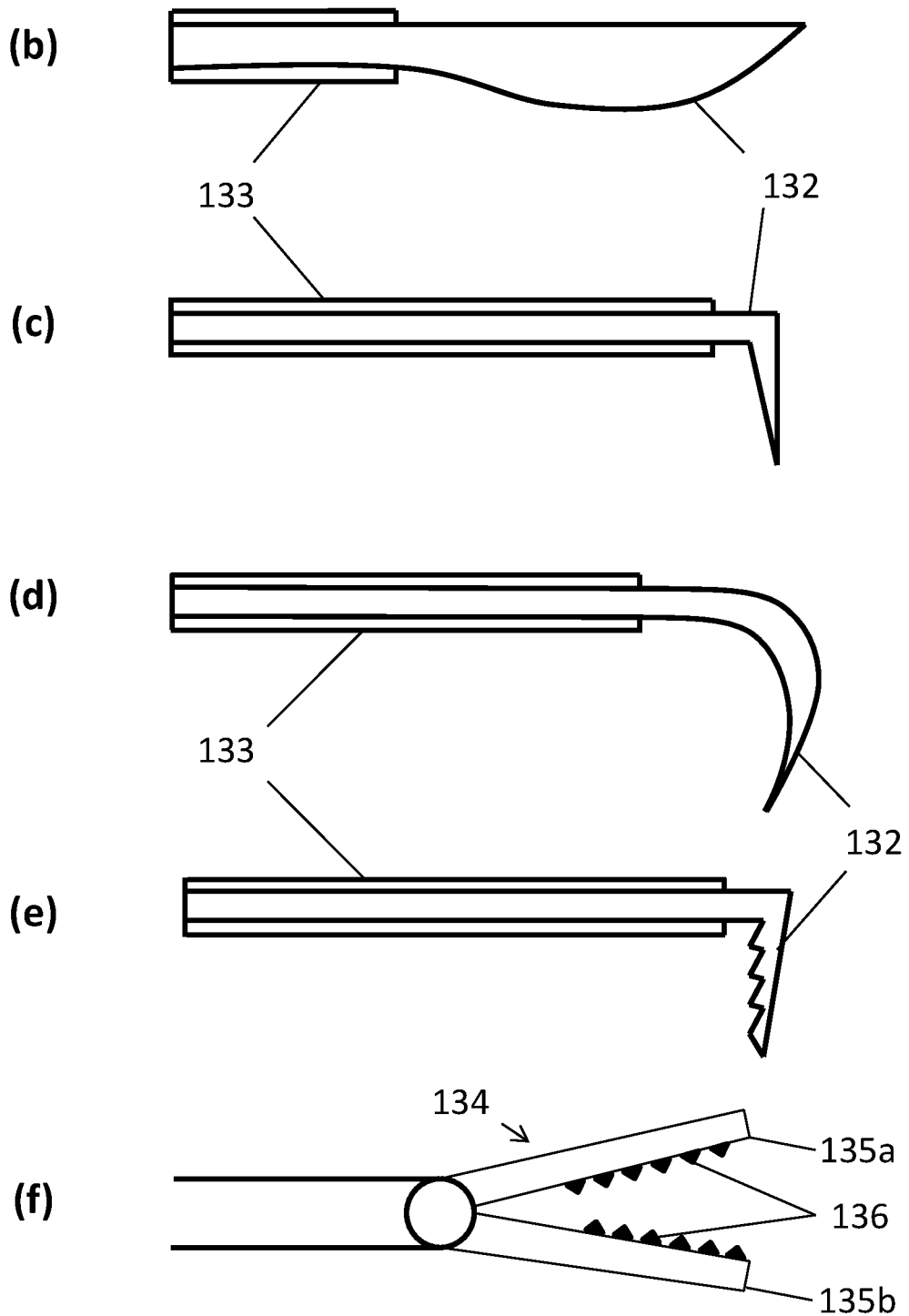

Referring to FIG. 1a of the drawings there is illustrated a surgical assembly 100 according to an embodiment of the present invention for use in a surgical procedure, such as an electrosurgical, ultrasonic or laser based surgical procedure. The assembly 100 comprises a first generator 110, such as a high voltage electrical generator capable of generating 1.5-20 kV, preferably 3-10 kV. The first generator 110 is arranged to generate a first signal which is preferably a direct current (DC) voltage waveform that is used for creating an electric field proximate a site of a surgical procedure. In an embodiment, the assembly 100 is arranged to receive via a connector 112, a second signal which is output from a second generator 120. The connector 112 may be disposed on a housing 111 of the first generator 110 and the second signal may be received within the housing 111. The second generator 120 may comprise a laser source (not shown) in which case, the second signal may comprise lasing radiation. Alternatively, the second generator 120 may comprise an ultrasonic wave generator, in which case the second signal may comprise an ultrasonic signal. In a further alternative, the second generator 120 may comprise an electrical generator for generating a radio frequency (RF) alternating current (AC) voltage waveform. In any of the above embodiments, the second signal is arranged to cut, seal and/or cauterize biological tissue of a patient during the surgical procedure.

The assembly 100 further comprises a surgical tool 130 which is electrically couplable with the first generator 110 and second generator 120, via a cable 140. The cable 140 comprises a connector 141 disposed at a distal end thereof for forming a connection with the first and second generator 110, 120, and as such may comprise an electrical connector, or a combination connector for forming an electrical and optical connection for example, to the respective generators. The cable 140 preferably comprises a length of at least 3 m so that the first and second generators 110, 120 can be kept isolated from the sterile environment of a surgical environment. In an embodiment, the connector 141 and cable 140 are arranged to communicate the first signal and the second signal to the tool 130 for use in performing the surgical procedure. However, in an alternative embodiment, it is to be appreciated that the first and second signals may be communicated to the tool 130 via separate cables and connectors (not shown). For the purposes of further describing the invention, only the embodiment in which the second generator 120 comprises an RF generator will be described.

In use, the tool 130 is held by a surgeon (not shown) to perform the procedure and comprises a housing 131, at least a portion of which forms a tool handle for the surgeon. The tool 130 further comprises a tool-piece 132 which may be detachably couplable with the housing 131 via a clamp or chuck arrangement (not shown). The tool-piece 132 is arranged to receive the first and second signals and is formed of an electrically conductive material, such as a metal, which extends through an electrically insulating sheath 133, whereas the housing 131 which is held by the surgeon is formed of an electrically insulating material, such as a dielectric.

The first signal is arranged to pass along a first circuit path and the second signal is arranged to pass along a second circuit path, and the first and second path is dependent on the electrosurgical mode of operating the tool 130.

Figure 2:
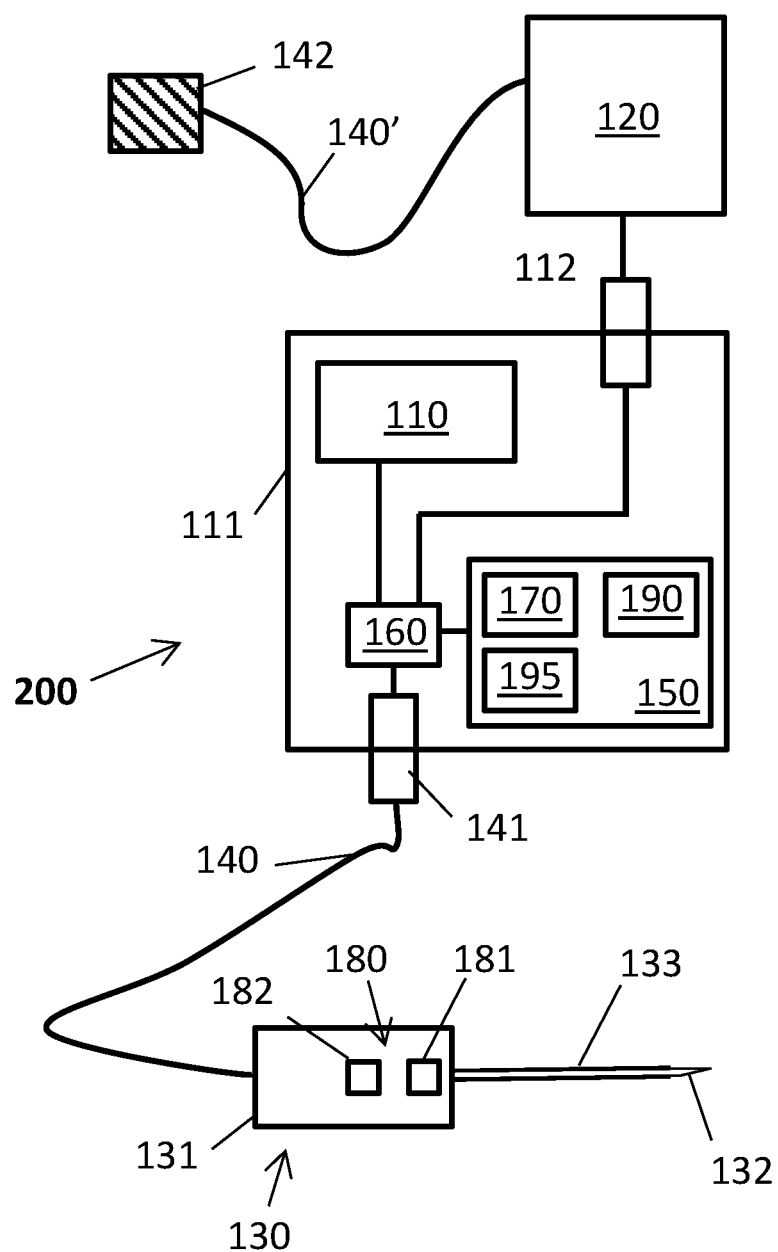
FIG. 2 is a schematic illustration of a surgical system according to an embodiment of the present invention.

For example, in a monopolar operational mode, as illustrated in FIGS. 1a and 2 of the drawings, the first signal is arranged to pass from a first electrical pole (not shown) of the first generator 110, through the patient to a second electrical pole of the first generator. The second electrical pole is electrically coupled to a patient (not shown) via a separate cable 140' which, in the arrangement illustrated in FIG. 1a, is coupled at a proximal end thereof to the second electrical pole (not shown) of the second generator 120 and at a distal end thereof to an adhesive pad 142 for forming a physical and electrical connection to the patient. The second electrical pole of the first generator 110 is electrically coupled to the second electrical pole of the second generator 120 (via cable 208' and connector 209—see later description relating to FIG. 4) and as such it is evident that the first and second path share a common cable 140' and adhesive pad 142. Accordingly, the first signal is arranged to pass from the first pole of the first electrical generator 110, along cable 140 to the tool-piece 132, whereupon electrons propagate from the tool-piece 132 toward the patient tissue, such as an abdominal wall of the patient owing to the electrical coupling of the patient to the second (i.e. opposite) electrical pole of the first generator 110 via cable 140'. The electrons and thus first signal subsequently passes back to the second pole of the first generator 110 via the adhesive pad 142 and further cable 140'. In a variation of the monopolar operational mode however, which is not illustrated, the proximal end of the cable 140' may instead by coupled directly to the second pole of the first generator 110. In this case, the first circuit path and second circuit path may comprise a dedicated return cable 140' and a dedicated adhesive pad 142 for forming an electrical contact with the patient, within their respective circuits.

The second signal is arranged to pass along a second circuit path which is again dependent on the particular electrosurgical mode of operating the tool 130. For example, in a monopolar configuration, as illustrated in FIGS. 1a and 2 of the drawings, the second signal passes between a first and second electrical pole (not shown) of the second generator 120, along a path comprising the cable 140, the tool-piece 132 and the cable 140' which is electrically coupled to the patient via the adhesive pad 142.

However, in a bipolar configuration (which is not illustrated), opposing electrical poles of the second generator 120 are electrically coupled to electrically isolated portions of the tool-piece 132. For example, in situations where the tool-piece 132 comprises a grasp or forceps 134 as illustrated in FIG. 1f, having opposing jaw portions, then the electrical poles of the second generator 120 may be separately electrically coupled with each jaw, and as such, there is no requirement for an electrical return via a pad 142 disposed on the patient. The second signal is arranged to pass from a first pole of the second generator 120, to one of the jaws 135a of the forceps 134 and then return to the second pole of the second generator 120 via the opposing jaw 135b of the forceps 134. The RF electrical field generated by the second generator 120 will thus become directed within the tissue held between the jaws 135a, 135b for performing the required cutting, sealing or cauterising of tissue. In this bipolar configuration, the cable 140' may be electrically coupled directly with the second pole of the first generator 110 and thus form part of the first circuit path only. In this case, the first signal is arranged to pass from the first pole of the first generator 110 to one of the jaws 135a, 135b of the forceps 134 and then return to the second pole of the first generator 110 via cable 140' and pad 142. However, the first signal would only be allowed to pass to one of the jaws 135a, 135b once the second signal has been removed from both jaws 135a, 135b and disconnected from the second generator, to otherwise prevent a first signal discharge between the jaws. Similarly, and as an extension to bipolar configurations, in multi-pole configurations, it would be necessary to remove the second signal from each pole, and disconnect the second generator 120 from each pole, before applying the first signal to one of the poles.

The assembly 100 further comprises a controller 150 for controlling the application of the first and second electrical signals to the tool-piece 132. The controller 150 may be disposed within the tool housing 131 for example or alternatively within the housing 111 of the first generator 110. The controller 150 is communicatively coupled with a switching assembly 160, and is arranged to control the switched state of the assembly 160 for switching the application of the first and second electrical signals to the tool-piece 132. The switching assembly 160 comprises a plurality of relays (R1-R6—see FIG. 4 of the drawings) which are opened and closed by a relay driver (not shown) in response to control signals from the controller 150 and in order to avoid any interference between the first and second signals, and the control signals, effective electrical shielding is disposed therebetween.

In an embodiment particularly suited to situations where the second signal comprises an ultrasonic or optical radiation signal, the controller comprises a sensing arrangement 170 for sensing the second signal. Such a sensing arrangement may be effected in a plurality of forms including but not limited to a medium wave antenna coupled to a diode detector for sensing an envelope of the peak electromagnetic field disturbance caused by the presence of the second signal, a combination of voltage or current transformer coupling a fractional sample of the second signal, or by a status input from a controller (not shown) of the second generator 120 indicative of the second signal being above or below an amplitude threshold which is communicated to the sensor arrangement 170. The sensing arrangement 170 is arranged to output a sensing signal to the controller 150 in dependence of the sensed second signal, to enable the controller 150 to control the application of the first electrical signal to the tool-piece 132 via the switching assembly 160. The controller 150 is arranged to apply the first electrical signal to the tool-piece 132 during a first time interval and the second electrical signal to the tool-piece during a second time interval, which is separate and non-overlapping with the first time interval. In this respect, the sensing arrangement 170 acts as a safety feature to prevent a simultaneous application of the first and second signal. The first interval corresponds to an interval during which the second signal is below a second threshold value and the second interval corresponds to an interval during which the first signal is below a first threshold value. The first and second threshold values correspond to signal values below which the first and second signals are unable to provide their surgical function of particulate clearing, and cutting, sealing or cauterizing, respectively. However, in embodiments in which the second signal comprises lasing radiation or an ultrasonic signal it is anticipated that the first and second signals may be applied to the tool-piece simultaneously.

In an embodiment, the assembly 100 further comprises at least one user controlled actuator 180. The controller 150 is arranged to control the application of the first and second signals to the tool-piece in response to the operational state of the actuator 180 and as such, the operational state of the actuator 180 determines in part, the control signals output by the controller 150 to the relay driver.

The actuator 180 may comprise a button 181, for enabling a surgeon to initiate an automated switching of the application of the first and second signals to the tool-piece 132. The button 181 may be mounted on the tool housing or comprise a foot-actuated button, or in the case of robotic surgery, located remote from the surgical site. It is envisaged that pressing button 181 will cause the second signal to pass to the tool-piece 132 for performing the surgical procedure, and upon releasing the button 181, the second signal will be removed from the tool piece 132. The release of the button 181 subsequently results in the application of the first signal to the tool-piece for smoke clearing.

In a further embodiment, the assembly 100 may comprise or further comprises an override actuator 182, such as a button on the housing of the tool-piece 132, for enabling the surgeon to activate the first signal for a desired period of time, once the second signal has been removed from the tool piece. For example, upon releasing button 181, then the second signal will be removed from the tool-piece and the first signal will subsequently be applied for a predetermined time. However, the override actuator 182 is arranged to enable the surgeon to continue to apply the first signal to the tool-piece 132. The application of the first signal to the tool-piece 132 by the override actuator 182 may be designed to continue while the button 182 is pressed, and/or to continue for a predetermined time following the release of the actuator 182. It is envisaged that this facility will be useful for surgeons who wish to clear large accumulations of suspended particles, including surgical smoke for example, without necessarily having to maintain operation of the actuator 182 throughout the clearing process. Such a time interval may be repeated by the surgeon as necessary by subsequent operation of the actuator 182.

However, to ensure a safe operation of the assembly 100, namely a safe application of the first and second signals, the controller 150 further comprises a timing arrangement 190 for timing the application of the first signal to the tool-piece 132 following a release of button 181. The timing arrangement 190 is arranged to receive notification of the removal of the second signal from the tool-piece, and is configured time the application of the first signal for a first time interval, such as 5s, after a predefined delay following the removal of the second signal from the tool-piece 132.

In a further embodiment, the assembly 100 further comprises at least one sensor (not shown) communicatively coupled with the controller 150, for sensing the presence of surgical particulates, and the at least one sensor is arranged to output a signal to the controller 150 representative of the amount of particulates surrounding the surgical site. In this embodiment, the controller 150 is arranged to suspend, and if necessary override any demand for the application of the second signal to the tool-piece 132 and thus maintain/initiate the application of the first signal to the tool-piece 132 for a dwell period/interval until the amount of surgical particulates have been reduced to a predefined threshold.

Figure 3:
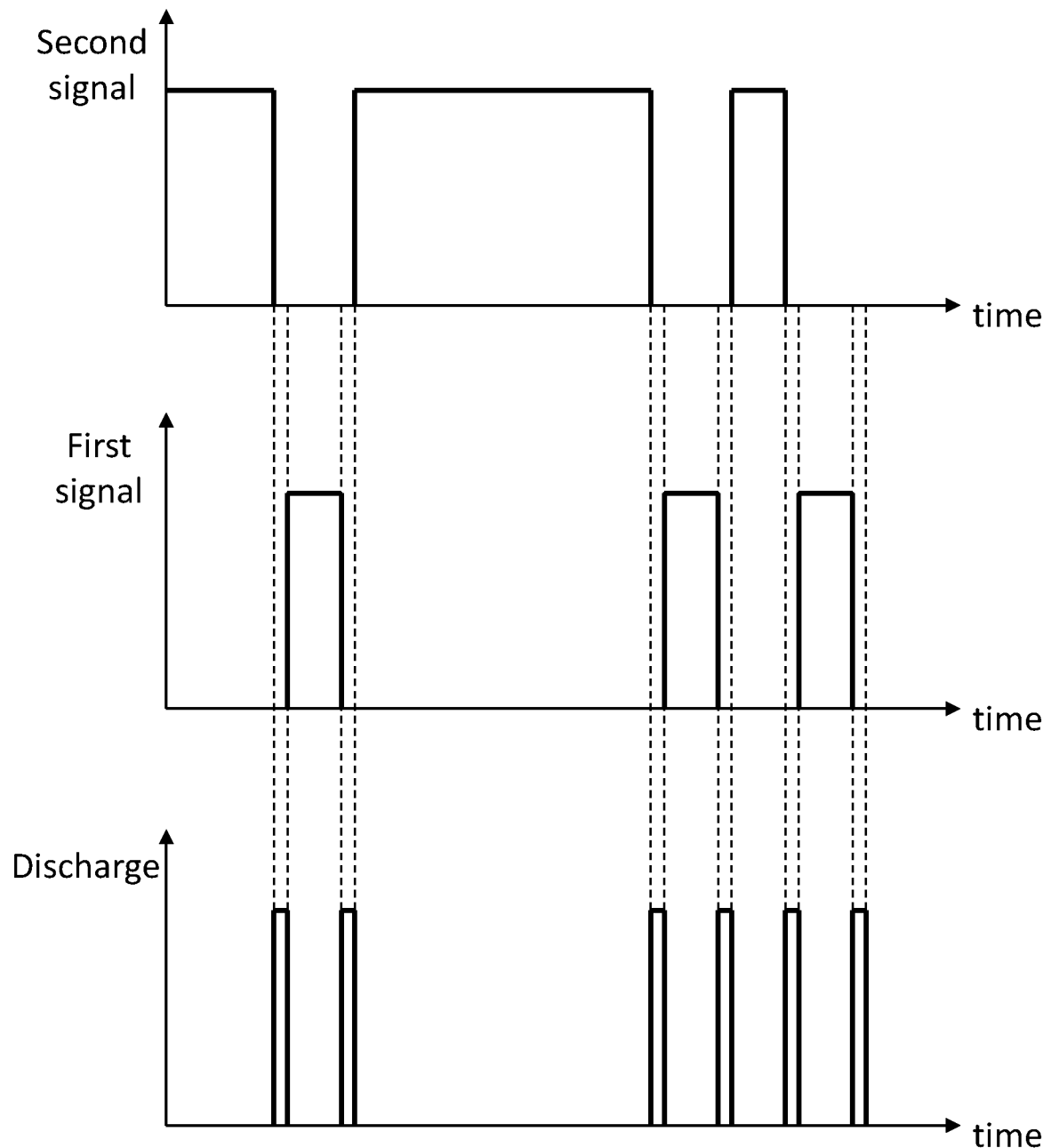
FIG. 3 is a graphical representation of a timing sequence for the first and second signals to the tool-piece.

The timing arrangement 190 and controller 150 are thus arranged to control the switching assembly 160 to delay the application of the first signal to the tool-piece 132, following the application of the second signal, by 10 ms-100 ms. For example, upon referring to FIG. 3 of the drawings, there is illustrated a timing sequence for the automated switching of the application of the first signal. Following the application of the second signal for a second time interval, as determined by the surgeon during a tissue cutting procedure for example, the circuit comprising the second generator 120 is allowed to discharge during a third time interval of approximately 10 ms-100 ms, before the first signal is applied for a first time interval of approximately 3 s, to clear particulates. Similarly, a further delay, namely a further third interval of 10 ms-100 ms is used to enable the circuit comprising the first generator 110 to discharge before the subsequent application of the second signal again. Such a delay in commencement of the first and second interval may avoid premature commutation of the tool-piece 132 between the second signal and the first signal where the envelope of the second signal is necessarily of a particularly intermittent nature, by enabling any residual first or second signal charge to discharge/dissipate (see later description relating to FIG. 4). It is known for instance that laser treatments intended for cutting, sealing or cauterizing tissue may be applied with significant dwell intervals where the second signal is below an amplitude threshold separated by intervals where the second signal is above the amplitude threshold. Such methods are also found on electrosurgical generators, and are generally employed to reduce collateral damage through thermal diffusion through tissue at the surgical site.

In a further embodiment, the controller 150 further comprises a proximity sensor 195 for sensing the separation of the distal end of the tool-piece 132 from an electrically conducting pathway, such as patient tissue. The proximity sensor comprises a voltage monitoring device (not shown) for monitoring the voltage at the distal end of the tool-piece 132. In the event that the distal end of the tool-piece 132 is sited too close to the abdominal wall (not shown), within the abdominal cavity of the patient for example, then the voltage will fall below a threshold value, owing to the reduced impedance between the tool-piece 132 and the patient tissue. This reduced voltage will be too low to create a suitable potential difference therebetween for ionising surgical particles and smoke. Moreover, in the event that the distal end of the tool-piece 132 is too close to the patient tissue, then this could result in a direct electrical short through the patient upon applying the first signal. Accordingly, the proximity sensor 195 is configured to prevent/terminate the application of the first signal in the event that the distal end of the tool-piece 132 is positioned or becomes positioned too close to the patient tissue.

The tool-piece 132 may comprise a linear spear-like shape (as illustrated in FIG. 1a of the drawings) having a pointed distal end 131. The pointed end acts as an ion-generating centre and facilitates the release of electrons therefrom when supporting the second signal, and thus the ionization of particles suspended in the local atmosphere of the surgical site. In alternative embodiments however, as illustrated in FIGS. 1b, 1c, 1d of the drawings, the tool-piece may comprise a blade configuration, an L or J-shape, and similarly comprise a pointed distal end. In yet a further embodiment as illustrated in FIG. 1e of the drawings, the tool-piece may comprise or further comprise a plurality of pointed serrations which extend along a portion of the length of the tool-piece for example. In a further embodiment, as illustrated in FIG. 1f of the drawings, the tool-piece may comprise opposing jaws 135a, 135b of a forceps 134, where one or both of the jaws 135a, 135b comprise sharp edges or serrations 136 which act as ion-generating centres and thus similarly facilitate the ionization of particles suspended nearby.

In use, the surgical assembly 100 is electrically coupled with the second electrical generator 120 via a socket 112 on the first electrical generator 110 to form a surgical system 200, an embodiment of which is illustrated in FIG. 2 of the drawings. An adhesive pad 142 is subsequently secured to the patient, such as upon a leg of the patient (not shown), and for a monopolar operation, the pad 142 is electrically coupled to the second pole of the second generator 120 via a cable 140'. However, as noted above, the second pole of the first and second generators may share the return cable 140' in this configuration, and as such, the second pole of the first generator 110 is also electrically coupled to the pad 142. To provide an enhanced electrical coupling to the patient, an electrically conductive gel (not shown) may be applied between the pad 142 and the patient's leg (not shown).

The surgical tool 130 is then electrically coupled with the first generator 110 via the cable 140 and associated connector 141 and a tool-piece 132 is secured within the tool 130 via the chuck arrangement (not shown) for example. The tool-piece 132 forms an electrical coupling with the cable 140, and a distal end of the tool-piece 132 is electrically exposed, namely extends out from the sheath 133, for performing the electrosurgical procedure. Once the tool-piece 132 has been secured in place, the first and second generators 110, 120 are activated via a respective power switch (not shown).

Figure 4:
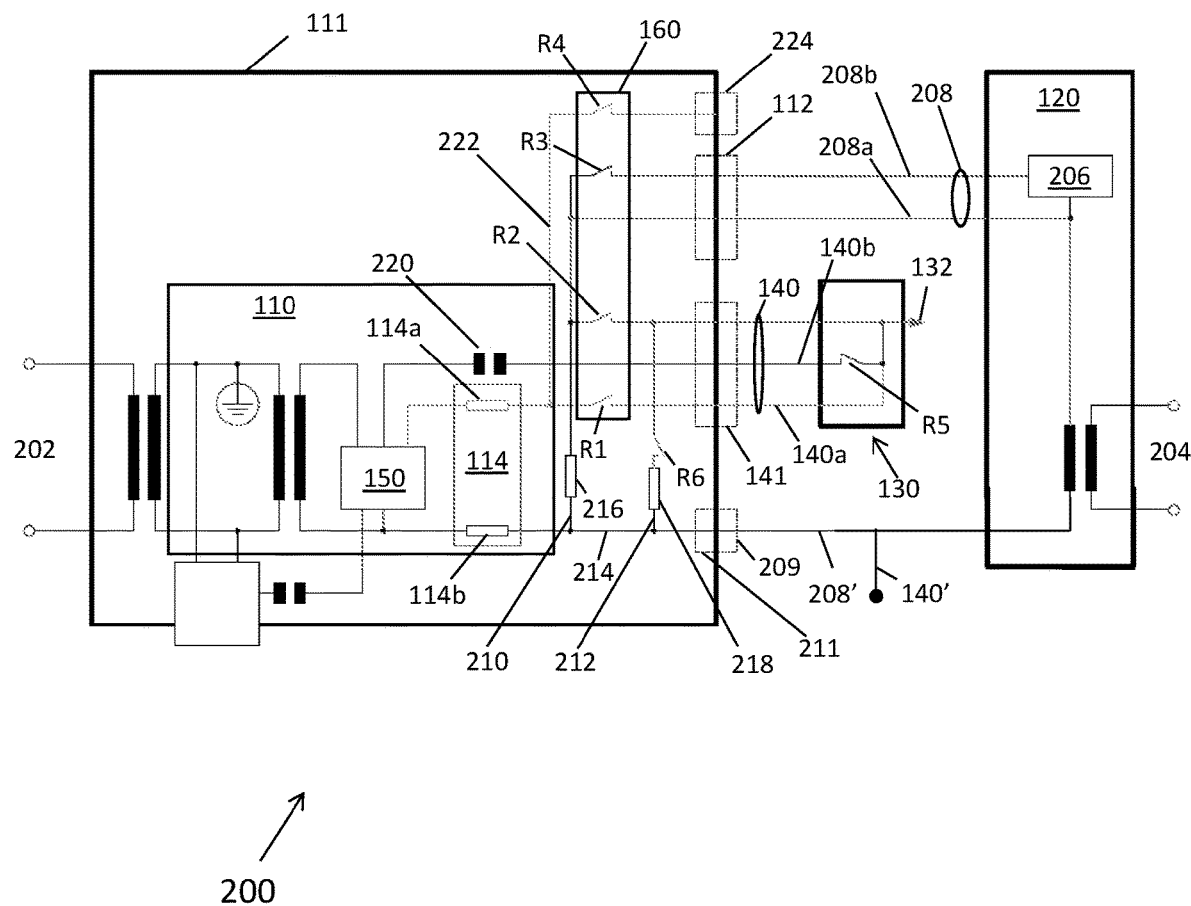
FIG. 4 is a schematic illustration of a circuit diagram of the surgical system illustrated in FIG. 2.

Referring to FIG. 4 of the drawings, there is provided a schematic illustration of a circuit diagram of the surgical system 200 configured for monopolar surgical operation. The system is arranged to receive ac mains electrical power via input terminals 202 and this ac mains is converted into dc using a rectification circuit (not shown) associated with the first generator 110. The high voltage output from the first generator 110 is provided to the hand-piece 130 via line 140a within cable 140. Line 140a comprises a relay R1 which forms part of the switching arrangement 160, and the application of the first signal to the tool-piece 132 is dependent on the switched state of this relay R1.

Figure 5:
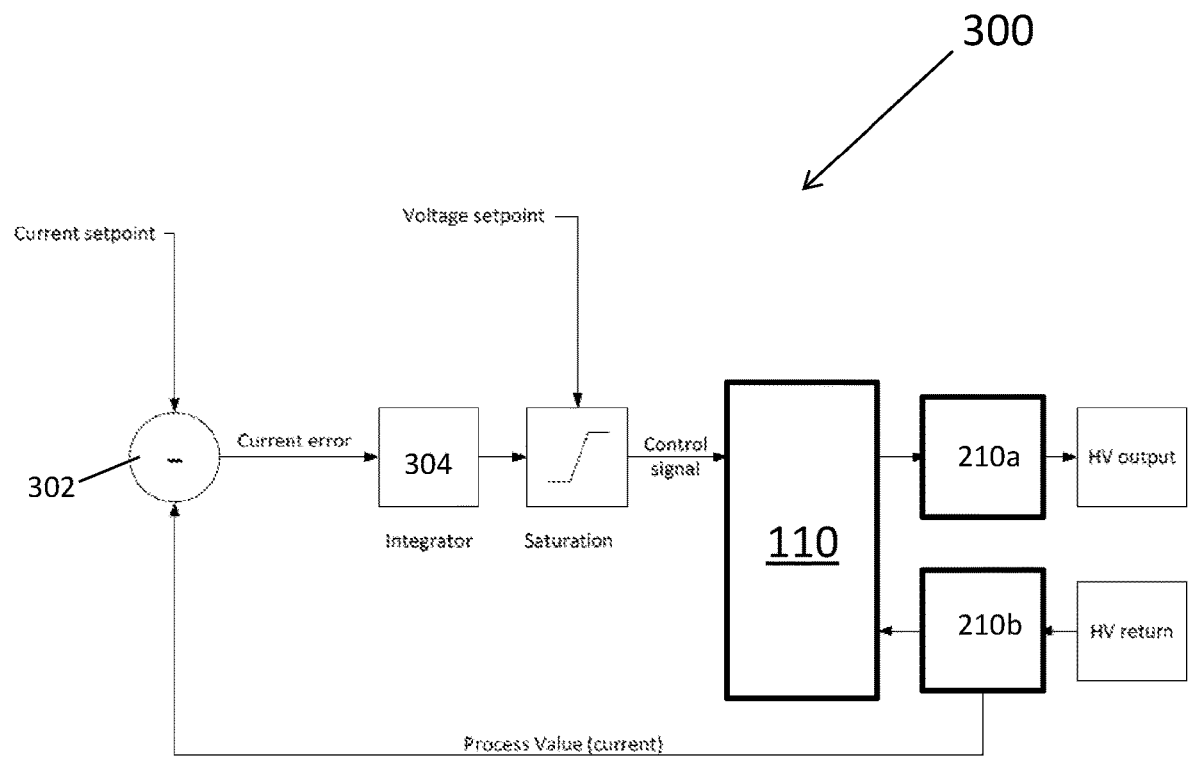
FIG. 5 is a schematic illustration of a circuit diagram illustrating the closed loop current control circuit.

Referring to FIG. 5 of the drawings, the first generator 110 comprises an analogue closed loop 300 for closed loop control of the output current. The operating current is influenced by the separation of the distal end of the tool-piece 132 from the patient tissue. As the tool-piece 132 approaches the patient tissue, the impedance falls. This causes the current to increase and the output voltage to fall. The first generator 110 however, monitors the current flowing between the tool-piece 132 and the patient tissue and terminates the current as it approaches an upper current limit, such as 10 µA, which is typically the maximum DC current that can safely be applied to a patient.

The control loop 300 primarily controls the output current of the first generator 110. The first generator 110 comprises a 200 MΩ series resistance 114 at the output thereof to ensure that a maximum current of 50 µA under a single short circuit fault condition, i.e. if the current limit fails and the first generator 110 outputs the maximum 10 kV. The resistance is embodied as two separate 100 MΩ resistors 114a, 114b, each separately connected in series with the high voltage and low voltage output terminals of the first generator 110. Electrical current is returned to the first generator 110 via a resistor 114b, thereby developing a voltage that is buffered and used as a process value. This value is compared with a current set point using a comparator 302 and the resulting error is integrated via integrator 304 providing a control signal for the first generator 110. If the process value is above/below the current set point, the control signal to the first generator 110 reduces/increases. This reduces/increases the high voltage output and increases/reduces the measured current toward the target set point value.

It is possible for the error signal to become saturated as the first generator output saturates at approximately 10 kV, thereby limiting the current available. The closed loop circuit 300 is designed to saturate at a variable level, allowing the output saturation voltage to be adjusted below 10 kV whenever the process value current is below the set point.

This output resistance 114 of the first generator 110 imposes an unwanted voltage drop at the output under normal operating conditions, creating a dependency between the voltage available at the output and the current being drawn. Practically, problems occur where the corona current is close to the typically 10 µA current limit. Voltage drop across the series resistance 114 reduces the output voltage below what is required for efficient corona, namely ionisation of smoke particulates. Smoke clearing performance is impaired by the mandated current limit, not because of insufficient current available, but because there is insufficient voltage.

Figure 6:
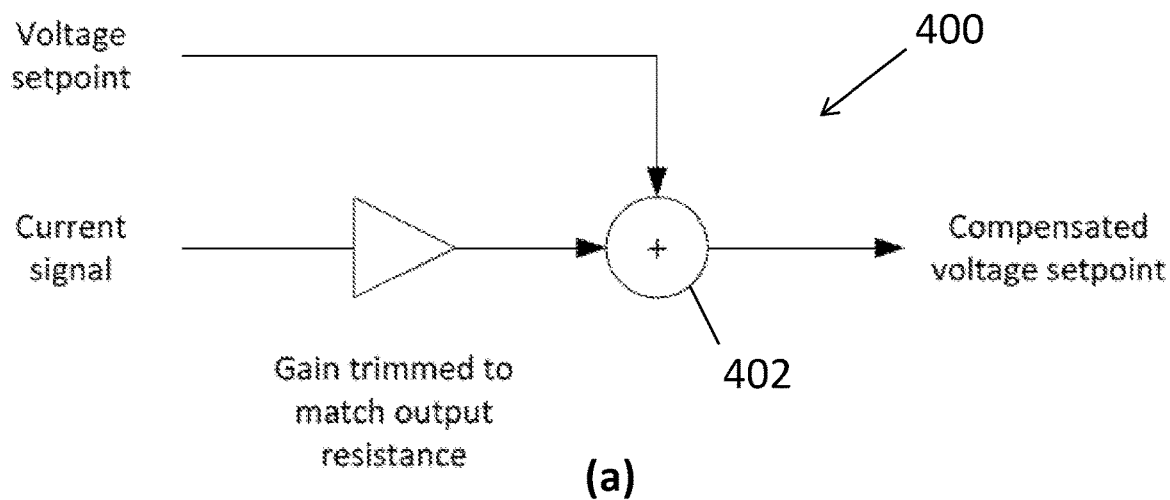
FIG. 6a is a schematic illustration of a voltage compensation circuit.
FIG. 6b is a graphical representation of the output voltage at the distal end of the tool-piece, as a function of electrical current.
Figure 6:
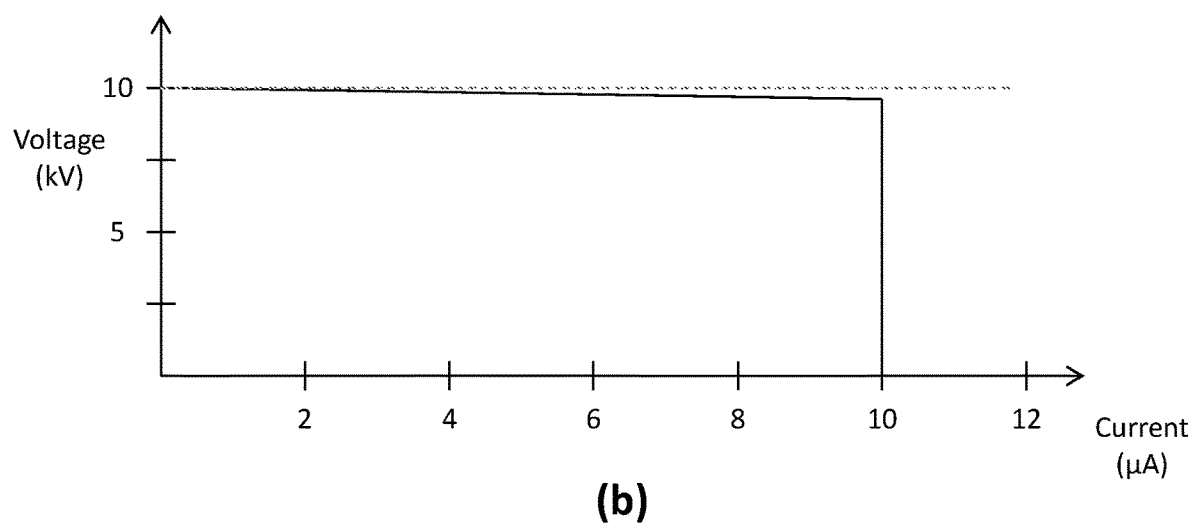

However, the voltage drop can be compensated using a voltage compensation circuit 400, as illustrated in FIG. 6a, which is configured to engineer a corresponding increase in the voltage output from the first generator 110. This is achieved by increasing the voltage set point by the voltage drop through the series resistance 114b. The circuit 400 comprises a processor or summation device 402 which is arranged to receive as input the desired or target voltage and a signal representative of an electrical current flowing through the resistor 114b. This current is already known by the closed loop control circuit 300; the process value of the control circuit 300 is representative of the current through the series resistance 114. Accordingly, by adding a proportion of the current signal to the set point achieves the desired voltage compensation. Operating the system 200 with this circuit 400 results in a near flat load curve where the voltage remains within 5% of the desired 10 kV voltage (as illustrated in FIG. 6b of the drawings), up to the current limit. This ensures that the ionisation efficiency no longer reduces with increasing current, provided that the first generator 110 has not reached the voltage saturation point.

Referring again to FIG. 4 of the drawings, the second generator 120 is similarly arranged to receive ac mains electrical power via input terminals 204 and generate a second signal which is output via an interface 206. The second signal is communicated to the hand-piece 130 and thus the tool-piece 132 via a cable 208 and connector 112. Cable 208 comprises a line 208a with a relay R2 disposed therein and a cable 208b with a relay R3 disposed therein. Cable 208 comprises a length which is minimized to reduce capacitance between the patient circuit and the environment, and also reduce capacitance between the poles of the second generator output. This tends to reduce RF leakage currents (and thus lower the risk of burns to the operator or patient) and reduce the risk of low frequency (mains) leakage current, which is an electrocution hazard, to the patient. On some systems, the RF displacement/capacitive currents which are increased by lengthening treatment cables are significant compared to surgical effect currents (surgical plasmas are often high impedances) and this results in an attenuation of the intended treatment waveform.

The system circuit further comprises a first and second electrical pathway 210, 212 coupled either side of relay R2 and which extend to a return or ground pathway 214. The pathway 214 extends to a terminal 211 on the housing 111. The second pole or return of the second generator 120 is electrically coupled to this pathway 214 via cable 208'. The cable 208' comprises a connector 209 disposed at a distal end thereof for electrically coupling with terminal 211. The first pathway 210 is electrically coupled at the high voltage side of relay R2 and comprises a series connected bleed resistor 216 (having a resistance value in the range of 1 MΩ-300 MΩ, and preferably 50 MΩ-200 MΩ) disposed therein. The bleed resistor acts to encourage the dissipation or discharge of residual charge arising from the application of the first signal. The resistance of the bleed resistor 216 is selected to suitably attenuate the residual portion of the first signal appearing across the output of the second generator 120 as the first signal is preferably limited to 10 µA. The bleed resistor 216 is a trivial addition to the loading presented to the second signal and as such, does not substantially affect the second signal. The second pathway 212 is electrically coupled at the low voltage side of the relay R2 and comprises a series connected relay R6 and a discharge resistor 218.

The circuit further comprises a relay R5 (which also forms part of the switching arrangement 160, although is located within the tool 130) disposed in the tool 130 which is manually activated by the surgeon, such as via button 181. The relay R5 is disposed in an electrical pathway 140b which extends within cable 140 to the controller 150 for communicating the surgeon demands. The pathway 140b further comprises an electrical isolation element, such as a capacitor 220 for preventing DC current flowing to the controller 150.

Upon referring to FIG. 4, the circuit further comprises a separate electrical pathway 222 which is electrically coupled to line 140a, and which extends to a port 224 disposed on the housing 111. Pathway 222 further comprises a series connected relay R4 which can be operated by the controller 150 to communicate the first signal to the port 224 in the event that a further electrode (not shown) is required to be electrically coupled to the first generator 110, for smoke clearing.

During an initialization process, relays R1 and R6 of the switching arrangement 160 are closed, with all other relays (R2-R5) of the switching arrangement 160 being open, so that any residual charge at the output of the first generator 110 is permitted to quickly discharge or dissipate across discharge resistor 218 for a period of 10 ms-100 ms. Following this initialization, relays R1 and R6 are opened, and relay R2 is closed to place the second generator 120 in a standby condition for performing the surgical procedure. During this standby period, any current leakage preferentially occurs across the bleed resistor 216, thereby minimizing current leakage across the other relays, R1, R3-R6.

When the surgeon demands the application of the second signal to the tool-piece 132 by actuating the button 181, relay R5 is closed, thereby instructing the controller 150 to close relay R3 (for the second time interval, as determined by the length of time the surgeon presses the button 181). During this second time interval the surgeon can manipulate the tool 130 to perform the surgical procedure. Upon releasing button 181, relay R5 is opened, which results in relay R3 opening stopping the second signal from passing to the tool-piece 132. Relay R2 is subsequently opened to disconnect the second generator 120 from the tool 130. Following a third time interval, relay R1 is closed by the controller 150 to apply the first signal to the tool-piece for smoke clearing (for a first time interval). The application of the first signal to the tool-piece 132 causes electrons to emanate from the distal end of the tool-piece 132 and any other ion-generating centres, and the electrons attach to the suspended particles thereby ionizing the particles. The electric field generated between the tool-piece 132 and the patient owing to the DC signal, subsequently causes the ionized particles to become attracted to the patient and thus away from the surgical site to improve the surgeons view thereof.

Following the first time interval, the system is configured to re-initialise. During this process, relay R6 is closed together with relay R1, with all other relays being open, so that any residual charge at the output of the first generator 110 is permitted to quickly discharge or dissipate across discharge resistor 218 for a period of 10 ms-100 ms.

In the case of a bipolar surgical operation or in situations where the second signal comprises an ultrasonic signal, bleed resistors 216 would be placed between the poles of the output of the second generator 120 and in a further alternative embodiment, such resistors would be placed between each pole of the second generator output and the patient return pad 142 or protective earth potential. In this further embodiment, the further resistors connected to protective earth would have values at least 50 MΩ so as to not compromise the floating status of the patient circuit, which comprises the electrical components coupled to the patient.

With any residual charge from the application of the first signal removed, relays R1 and R6 are subsequently opened, and relay R2 is closed to place the second generator 120 in a standby condition again, ready for a further demand for the second signal from the surgeon.

From the foregoing it is evident that the assembly 100 and system 200 enable a surgeon to cut patient tissue with a tool-piece 132 and also remove particles generated from the cutting procedure with the same tool-piece 132. The assembly 100 and system 200 thus provide for a more compact and functional surgical tool which reduces surgical trauma and improves usability.

The invention claimed is:

1. A surgical assembly comprising a switching assembly which is arranged to receive a DC signal for use in generating an electrical field proximate a site of a surgical procedure for ionizing and removing particles suspended proximate the surgical site, and a second signal for use in cutting, sealing or cauterizing tissue of the patient during the surgical procedure, the surgical assembly further comprising a surgical tool comprising a tool-piece, the switching assembly being arranged to switch the application of the DC signal and the second signal to the tool-piece, and a controller for controlling the switching assembly to control the application of the DC signal to the tool-piece during a first time interval and the application of the second signal to the tool-piece for a second time interval, the DC and second signals being separated by a third interval of 10-100 ms during which the DC and second signals are removed from the tool-piece, wherein the controller comprises a timing arrangement configured to time the application of the DC signal to the tool-piece following the second interval, such that the first and second intervals are non-overlapping intervals, wherein the timing arrangement is arranged to time the application of the DC signal in dependence of a cessation of the second signal, wherein any residual capacitive charge accumulated during the preceding first interval is allowed to discharge or dissipate during the third interval, the surgical assembly comprises at least one resistor for enabling the discharge or dissipation of the residual charge, and the controller further comprises a sensing arrangement for sensing the second signal, the sensing arrangement being arranged to output a sensing signal to the controller in dependence of the sensed second signal to prevent simultaneous application of the DC and second signals.

2. The surgical assembly according to claim 1, wherein the controller comprises an override actuator for applying the DC signal to the tool-piece.

3. The surgical assembly according to claim 1, wherein the switching assembly comprises at least one relay for switching the application of the DC and second signals to the tool-piece.

4. A surgical system comprising the surgical assembly according to claim 1, a first generator for generating the DC signal for use in generating an electrical field proximate a site of a surgical procedure for removing particles suspended proximate the surgical site, and a second generator for generating the second signal for use in cutting or cauterizing tissue of the patient during the surgical procedure.

5. The surgical assembly according to claim 4 further comprising a voltage compensation circuit for maintaining a substantially constant voltage difference between a distal end of the tool-piece and patient tissue independently of a separation between the tool-piece and the patient tissue.

6. The surgical assembly according to claim 5 wherein the voltage compensation circuit comprises a resistor arrangement electrically couplable with an output of the first generator, and a processor which is arranged to receive as input a target voltage and a signal representative of an electrical current flowing through the resistor arrangement, the processor being arranged to process the signal and increase the voltage output from the first generator by an amount corresponding to a voltage drop across the resistor arrangement.

7. The surgical assembly according to claim 4, further comprising an analogue closed loop circuit for closed loop control of the current output from the first generator.

8. The surgical assembly according to claim 7, wherein the analogue closed loop circuit is arranged to limit the current flowing from the first generator to a maximum value of 100 μA.

9. A process for applying a DC signal and a second signal to a tool-piece, the DC signal being for use in generating an electrical field proximate a site of a surgical procedure for removing particles suspended proximate the surgical site, and the second signal being for use in cutting, sealing or cauterizing tissue of the patient during the surgical procedure, the process comprising applying the DC signal to the tool-piece during a first time interval and applying the second signal to the tool-piece for a second time interval, the DC and second signals being separated by a third interval of 10-100 ms during which the DC and second signals are removed from the tool-piece, the process comprising timing the application of the DC signal to the tool-piece following the second interval, such that the first and second intervals are non-overlapping intervals and such that the DC signal is applied in dependence of a cessation of the second signal and wherein any residual capacitive charge accumulated during the preceding first or second interval is allowed to discharge or dissipate during the third interval via at least one resistor, the process comprising sensing the second signal and outputting a sensing signal in dependence of the sensed second signal to prevent simultaneous application of the DC and second signals.

* * * * *